(12) United States Patent
Fattinger (10) Patent No.: US 9,405,069 B2
(45) Date of Patent: Aug. 2, 2016

(54) METHOD FOR PREPARING AN OUTER SURFACE OF A PLANAR WAVEGUIDE TO BE CAPABLE OF BINDING TARGET SAMPLES ALONG A PLURALITY OF PREDETERMINDED LINES AND A PLANAR WAVEGUIDE

(71) Applicant: Hoffmann-La Roche Inc., Nutley, NJ (US)

(72) Inventor: Christof Fattinger, Blauen (CH)

(73) Assignee: HOFFMANN-LA ROCHE INC., Nutley, NJ (US)

(*) Notice: Subject to any disclaimer, the term of this patent is extended or adjusted under 35 U.S.C. 154(b) by 0 days.

(21) Appl. No.: 14/655,923

(22) PCT Filed: Jan. 17, 2014

(86) PCT No.: PCT/EP2014/050902
§ 371 (c)(1),
(2) Date: Jun. 26, 2015

(87) PCT Pub. No.: WO2014/111521
PCT Pub. Date: Jul. 24, 2014

(65) Prior Publication Data
US 2015/0338579 A1    Nov. 26, 2015

(30) Foreign Application Priority Data

Jan. 17, 2013   (EP) .................................... 13151646

(51) Int. Cl.
*G02B 6/036* (2006.01)
*G02B 6/26* (2006.01)
(Continued)

(52) U.S. Cl.
CPC ............ *G02B 6/26* (2013.01); *G01N 33/54353* (2013.01); *G01N 33/54373* (2013.01); *G01N 33/54393* (2013.01)

(58) Field of Classification Search
None
See application file for complete search history.

(56) References Cited

U.S. PATENT DOCUMENTS

| 6,753,131 B1 | 6/2004 | Rogers et al. |
| 7,212,693 B2 * | 5/2007 | Carr ....................... G01N 21/45 385/12 |

(Continued)

FOREIGN PATENT DOCUMENTS

WO      WO 92/10092 A1     6/1992

OTHER PUBLICATIONS

International Search Report Issued in PCT/EP2014/050902 on Jul. 24, 2014.
(Continued)

*Primary Examiner* — Rhonda Peace
(74) *Attorney, Agent, or Firm* — Mintz Levin Cohn Ferris Glovsky and Popeo, P.C.

(57) ABSTRACT

According to the invention there is provided a method for preparing the outer surface (11) of the planar waveguide (1) for binding target samples along the plurality of predetermined lines (4). The method comprises the following steps. Providing a planar waveguide (1) with an outer surface (11) adapted for attachment of a head group (21) of a linker molecule (2) to the outer surface (11). Sequentially applying at least one plurality of linker molecules (2, 5) to the outer surface (11). Each plurality of the at least one plurality of linker molecules (2, 5) assembles to form an individual layer of linker molecules (2, 5) with individual layers formed one above the other starting from the outer surface (11) of the planar waveguide (1). Each linker molecule (2, 5) comprises a functional group (22, 52) and the head group (21, 51) which is capable of attaching to the outer surface (11) of the planar waveguide (1) or to the functional groups (22) of the preceding layer of linker molecules (2). The functional groups (52) of the plurality of linker molecules (5; 2) of the uppermost layer are bound to photo-labile protecting groups (3) so that each functional group (52) bound to a said photo-labile protecting group (3) is incapable of attaching a complementary functional group of a further molecule. Exposing those photo-labile protecting groups (3) of the uppermost layer arranged along a plurality of predetermined lines (4) to light of a predetermined wavelength to remove the exposed photo-labile protecting groups (3) from the functional groups (52) to make these functional groups (52) capable of attaching a complementary functional group of a further molecule.

16 Claims, 6 Drawing Sheets

(51) Int. Cl.
*G01N 33/543* (2006.01)
*G02B 6/34* (2006.01)

(56) References Cited

U.S. PATENT DOCUMENTS

| | | | | |
|---|---|---|---|---|
| 7,214,530 | B2* | 5/2007 | Sayre | G01N 33/54373 422/50 |
| 7,223,534 | B2* | 5/2007 | Kaylor | B82Y 30/00 356/451 |
| 2002/0137096 | A1 | 9/2002 | Fodor et al. | |
| 2002/0182603 | A1 | 12/2002 | Chapman et al. | |
| 2003/0017464 | A1 | 1/2003 | Pohl | |
| 2003/0032043 | A1 | 2/2003 | Pohl et al. | |
| 2005/0250141 | A1* | 11/2005 | Lambert | B82Y 5/00 435/6.11 |
| 2006/0057729 | A1 | 3/2006 | Moon et al. | |
| 2009/0305437 | A1* | 12/2009 | Allemand | B82Y 10/00 438/1 |
| 2015/0276612 | A1* | 10/2015 | Fattinger | G01N 21/47 422/69 |
| 2015/0338579 | A1* | 11/2015 | Fattinger | G01N 33/54353 385/129 |

OTHER PUBLICATIONS

Michael Pawlak et al. "Zeptosens' protein microarrays: A novel high performance microarray platform for low abundance protein analysis." Proteomics 2002, 2, 383-393.
Getachew Tizazu et al. "Large area nanopatterning of alkylphosphanoate self-assembled monolayers on titanium oxide surfaces by interferometric lithograph." Nanoscale, vol. 3. (2011): 2511-2516.
Brigitte M. Städler et al. "Light-Induced in Situ Patterning of DNA-Tagged Biomolecules and Manoparticles." vol. 5, No. 3 (2006): 215-219.
Stefan Lofas. "Dextran modified self-assembled monolayer surfaces of use in biointeraction analysis with surface plasmon resonance." Pure and Applied Chemistry. vol. 67 No. 5, (1995): 829-834.
Stefan Lofas et al. "A Novel Hydrogel Matrix on Gold Surfaces in Surface Plasmon Resonance Sensors for Fast and Efficient Covalent Immobilization of Ligands." J. Chem. Soc., Chem. Commun., 1990 1526-1528.
Kasper Renggli et al. "Selective and Responsive Nanoreactors." Advanced Functional Materials 2011, 21, 1241-1259.
Mariusz Grzelakowski et al. "Immobilized Protein-Polymer Nanoreactors." Small vol. 5 No. 22 (2009) 2545-2548.
T.J. Suleski et al. "Fabrication of high-spatial-frequency gratings through computer-generated near-field holography." Optics Lettes vol. 24, No. 9 (1999) 602-604.
Pasi Laakkonen et al. "Coated phase masks for proximity printing of Bragg gratings." Optics Communications. 192 (2001) 153-159.
John A. Rogers et al. "Generating 90 nanometer features using near-field contact-mode photolithography with an elastomeric phase mask." J. Vac. Sci. Technol. B 16(1) (1998) 59-68.
T.J. Suleski et al. "Fabrication of optical microstructures through fractional Talbot imaging." Micromachining Technology for Micro-Optics and Nano-Optics III. vol. 5720 86-93.
William B. Case et al. "Realization of optical carpets in the Talbot and Talbot-Lau configurations." Optics Express. vol. 17, No. 23 (2009).
R. Hofer et al. "Alkyl Phosphate Monolayer, Self-Assembled from Aqueous Solution onto Metal Oxide Surfaces." Langmuir vol. 17 (2001)4014-4020.
Doris M. Spori et al. "Influence of Alkyl Chain Length on Phosphate Self-Assembled Monolayers." Lagmuir vol. 23 (2007) 8053-8060.
Marcus Textor et al. "Structural Chemistry of Self-Assembled Monolayers of Octadecylphosphoric Acid on Tantalum Oxide Surfaces." Langmuir. vol. 16 (2000) 3257-3271.
S. Tosatti et al. "Self-Assembled Monolayers of Dodecyl and Hydroxy-dodecyl Phosphates on Both Smooth and Rough Titanium and Titanium Oxide Surfaces." Langmuir. vol. 18 (2002) 3537-3548.
Milan Mrksich et al. "Using Self-Assembled Monolayers to Understand the Interactions of Man-made Surfaces With Proteins and Cells." Annual Reviews Biophys. Biomol. Struct.1996, 25: 55-78.
Dominik Woll et al. "Diffusion-controlled sensitization of photocleavage reactons on surfaces." Phtochem. Photobiol. Sci., 2012, 11, 533-538.
Dominik Woll et al. "Triplet-Sensitized Photodeprotection of Oligonucleotides in Solution and on Microarray Chips." Helvetica Chimica Acta. vol. 87 (2004) 28-45.
Glenn McGall et al. "Light-directed synthesis of high-density oligonucleotide arrays using semiconductor photoresists." Proc. natl. Acad. Sci. USA. vol. 96 (1996) 13555-13560.

* cited by examiner

METHOD FOR PREPARING AN OUTER SURFACE OF A PLANAR WAVEGUIDE TO BE CAPABLE OF BINDING TARGET SAMPLES ALONG A PLURALITY OF PREDETERMINDED LINES AND A PLANAR WAVEGUIDE

RELATED APPLICATION

This application is a national stage application, filed under 35 U.S.C. §371, of International Application No. PCT/EP2014/050902 filed on Jan. 17, 2014, which claims priority to European Patent Application No. 13151646.0 filed on Jan. 17, 2013, the contents of which are hereby fully incorporated by reference.

The present invention relates to a method for preparing an outer surface of a planar waveguide to be capable of binding target samples along a plurality of predetermined lines as well as to a planar waveguide in accordance with the respective independent claim.

In remote technical fields which are not related to waveguides, the patterning of nanostructures on metal surfaces, like native titanium, is known (e.g., "Getachew Tizazu et al., Large area nanopatterning of alkylphosphonate self-assembled monolayers on titanium oxide surfaces by interferometric photo-lithography", Nanoscale, 2011, 3, 2511, Published on Mar. 23, 2011 on http://pubs.rsc.org, doi: 10.1039/CONR00994F). Metals are generally not suitable to form a planar waveguide. The preparation of metal surfaces provides no hint for the preparation of an outer surface of a planar waveguide. In particular, native titanium is no material suitable for being used in a planar waveguide.

The field of application of the present invention is the detection of binding events. Well known devices detect binding events of a target sample with a capture molecule by use of labels which are capable of emitting fluorescent light upon excitation. For example, fluorescent tags can be used as labels for labelling the target samples. Upon excitation, the fluorescent tags are caused to emit fluorescent light having a characteristic emission spectrum. The detection of this characteristic emission spectrum at a particular spot indicates that the labelled target molecule has bound to the particular type of capture molecule present at the respective particular spot on the outer surface of the planar waveguide. A sensor for detecting labelled target samples is described in the article "Zeptosens' protein microarrays: A novel high performance microarray platform for low abundance protein analysis", Proteomics 2002, 2, S. 383-393, Wiley-VCH Verlag GmbH, 69451 Weinheim, Germany.

A novel device for the optical detection of binding events provides an advantageous way to overcome the need of labels by directly detecting the presence of target samples at capture molecules. The device comprises a planar waveguide into which light is coupled by an optical coupler such that coherent light propagates through the planar waveguide with an evanescent field of the coherent light propagating along an outer surface of the planar waveguide. The outer surface of the planar waveguide is prepared so as to be capable of binding target samples along a plurality of predetermined lines such that light of the evanescent field is scattered by target samples arranged along the plurality of predetermined lines. The scattered light constructively interferes in a predetermined detection location so as to contribute to a detectable signal from the superimposed scattered light from the target samples.

This novel device achieves an high detection sensitivity by superposition of coherent light scattered at target samples arranged along the plurality of predetermined lines, this physical phenomenon is referred to as "diffraction". The scattered light interferes constructively, for example, in a predetermined detection location to a maximum in intensity since the lines of the plurality of predetermined lines are arranged so that light scattered at target samples on different lines has in the predetermined detection location a difference in optical path length of a multiple integer of the wavelength of light propagating through the planar waveguide. The predetermined detection location is to be arranged with respect to the plurality of predetermined lines to meet the requirements of constructive interference. In further examples the light diffracts at the plurality of predetermined lines so as to interfere in predetermined directions in the planar waveguide.

Therefore, it is an object of the invention to provide a method for preparing an outer surface of a planar waveguide to be capable of binding target samples along a plurality of predetermined lines. A still further object of the invention is to provide a planar waveguide with a prepared outer surface of the planar waveguide to be capable of binding target samples along the plurality of predetermined lines.

Advantageous embodiments of the method according to the invention are the subject of the respective dependent claims.

According to the invention there is provided a method for preparing an outer surface of a planar waveguide to be capable of binding target samples along a plurality of predetermined lines. The method comprises the following steps.

Provide a planar waveguide which has an outer surface adapted for attachment of a head group of a linker molecule to the outer surface.

Thereafter, sequentially apply at least one plurality of linker molecules to the outer surface. Each plurality of the at least one plurality of linker molecules assembles to form an individual layer of linker molecules with individual layers being formed one above the other starting from the outer surface of the planar waveguide. Each linker molecule comprises at least one functional group and a head group which is capable of attaching to the outer surface of the planar waveguide or to the functional groups of the preceding layer of linker molecules through formation of a covalent bond or absorbed via electrostatic interaction. The functional groups of the plurality of linker molecules of the uppermost layer are attached to photo-labile protecting groups so that each functional group protected by a said photo-labile protecting group is incapable of attaching a complementary functional group of a further molecule.

Then, expose those photo-labile protecting groups of the uppermost layer arranged along a plurality of predetermined lines to light of a predetermined wavelength to remove the exposed photo-labile protecting groups from the functional groups to make these functional groups capable of attaching a complementary functional group of a further molecule.

As a result, the removal of the exposed photo-labile protecting groups from the functional groups defines the geometrical locations of these functional groups which are capable of attaching a complementary functional group of a further molecule. The locations of the functional groups is chosen to be the plurality of predetermined lines. As described in the introductory part, coherent light scattered at target samples on those lines constructively interferes in a predetermined detection location. Technically preferred is the arrangement on a plurality of predetermined curved lines having a decreasing distance between adjacent lines. The arrangement of curved lines with a decreasing distance between adjacent lines allows to focus the diffracted light into a predetermined detection location. The arrangement of the plurality of predetermined curved lines includes the repeated arrangement of a series pluralities of predetermined lines one above each other so as to provide further separate foci (e.g. by slightly rotating each subsequent plurality of predetermined lines with respect to the preceding plurality of predetermined lines). Each of the series of pluralities of predetermined lines can be of a different chemical, biological or pharmaceutical characteristic. Alternatively preferred is the arrangement on straight lines so as to diffract the light within the plane of the planar waveguide in which diffracted light interferes in predetermined directions within the planar waveguide. The exposure of those photo-labile protecting groups arranged along a plurality of predetermined lines can be carried out entirely (ideally all photolabile protecting groups are removed) or partially (a predetermined portion of the photo-labile protecting groups are removed, e.g. 10%, 20%) with various photo-lithographic methods (e.g. contact mode or far-field photo-lithography), but is preferably carried out by near-field photo-lithography in which the photo-lithographic mask has no contact to the waveguide but forms a small gap between the mask and the outer surface of the waveguide (respectively the exposed photo-labile protecting groups of the linker molecules which can be filled with a liquid during exposure of the photo-labile protecting groups on the linker molecules attached to the outer surface of the waveguide). The exposure in photo-lithographic methods includes the use of photo-lithographically produced tools, like an elastomeric phase mask for near-field contact mode photophoto-lithography, as described in detail in John A. Rogers et al., Generating ~90 nanometer features using near-field contact-mode photophoto-lithography with an elastomeric phase mask, J. Vac. Sci. Technol. B 16(1), January/February 1998, page 59 et seq.

The sequential application of the at least one plurality of linker molecules includes two preferred examples which are described further below. In one variant, one plurality of linker molecules is applied directly to the outer surface of the planar waveguide which assemble in a single individual layer. In another variant, a first plurality of linker molecules is applied to the outer surface and subsequently a second plurality of linker molecules is applied thereto so that they assemble in just two individual layers one above the other. In each example, the functional groups of the linker molecules assembled in the uppermost layer of linker molecules is bound to photo-labile protecting groups. This can be achieved before or after application of the uppermost plurality of linker molecules. The uppermost layer, or in other words the outermost layer, allows the arrangement of a photo-lithographic mask so that the uppermost layer can be photo-lithographically illuminated directly therethrough.

"Molecules" within the meaning of the present application includes a wide range of meanings, but is in principle the affiliation of two or more atoms which are bound together by chemical bonds. The type and number of atoms is not limited, wherein the term molecules explicitly includes the composition of two and more molecules. The term molecule is not limited to specific types of inter and intra molecular bindings as well as to specific chemical, pharmaceutical or physical characteristics. In particular, macromolecules and molecular assemblies are explicitly included in the term (e.g. polymers, oligonucleotides, nucleic acids, proteins, liposomes and peptides). Principally, the term molecule stands for any synthetic or natural stable polyatomic affiliation.

It is to be understood, that within the scope of the invention, chemical bonds may be replaced by any other stable specific assembly of molecular interactions like ionic interaction, hydrophobic interaction, complex formation, hydrogen bonding, fluorous phase formation and the like, as known to an expert in the field.

"Functional groups" within the meaning of the present application are moieties (sections of molecules) and molecules (including biomolecules) to which a specific moiety or molecule, in particular a complementary functional group of a further molecule, can bind. For example a linker molecule comprises at least one functional group. Examples of functional groups are ordinary functional group such as amino-, carboxylic acid-, carboxylic acid ester, thioester, hydroxyl-, mercapto-, boronic acid-, alkyne-, azido-, cyclooctyne-, maleinimido-, iodacetyl-, aldehyde-, keto-, hydroxylamino-, cyano-, epoxy-, sulfonic acid groups. Other examples are bisfunctional groups like a vicinal diol, an aromatic ortho dialdehyde or a alpha mercapto amino alkane (eg an N terminal Cystein) and an organic or peptidic metal chelate adsorbent such as nitrilotriacetic acid (NTA) or poly-histidine forming stable complexes with $Ni^{2+}$, a single stranded DNA, streptavidin, biotin, a receptor or its ligand. Further examples of functional groups are "tags" which are recognized by enzymes to form a covalent bond, between a tag and a complementary "tag". Examples are Snap tag, Clip tag, and the Sortase tag.

Multiple interactions of many functional groups of the plurality of the linker molecules and complementary functional groups of a further molecule are also included. Multiple interactions could be covalently and non covalently and does also include hydrophobic interaction, which means that the term functional group does also include hydrophobic moieties capable of interacting with hydrophobic entities of the further molecule.

Therefore all kinds of interactions of functional groups and complementary functional groups which result in immobilization of a further molecule are included.

A "further molecule having a complementary functional group" is within the meaning of the present application the capture molecule, the modified capture molecule or a linker molecule comprising a head group of the applied further plurality of linker molecules. A complementary functional group is capable of reacting or interacting with a functional group of linker molecules.

A "complementary functional group" within the meaning of the present application is a moiety (a section of a molecule), a molecule or a biomolecule to which a specific moiety or molecule can bind. For example, the complementary functional group of a further molecule is a head group of a linker molecule as well as a section of a capture molecule capable of binding to the functional group of a linker molecule of the preceding layer. For example, complementary single stranded DNA can form a double helix by hydrogen bonding to carry out orthogonal coupling chemistry. Another option is to form a stable non covalent bond by the use of protein ligand interactions. Examples of complementary functional groups are ordinary functional group such as $NH_2$—, COOH—, OH—, SH—, sulfonic acid, an organic or peptidic metal chelate adsorbent such as nitrilotriacetic acid (NTA) or poly-histidine forming stable complexes with $Ni^{2+}$, a single stranded DNA, streptavidin, biotin, a receptor or its ligand. In general, the complementary functional groups may be of the same type as the functional group so that the mentioned examples of functional groups apply to complementary functional groups.

"Capture molecules" are any type of pharmaceutical, biological or chemical molecular target to which a target sample may bind for the detection of binding events. For example biological receptors, proteins, liposomes, nanoreactors, etc.

In general, a "target sample" is a target molecule in a sample which may bind to the capture molecule for the detection of binding events.

"Bind" and "binding event" within the meaning of the present application includes any kind of molecular recognition, and any kind of molecular interaction between any kind of a capture molecule or a binding site thereof and any kind of target sample. This includes actual binding of two or more binding partners as well as the accumulation of bio molecular interaction partners (tar lipo having a channel protein).

The term "attach" is used similar to coupling and relates in general to each type of chemical or physical attachment (or coupling) so that one molecule (e.g. the head group of the linker molecule or the capture molecule) is attached to the outer surface of the planar waveguide or to the functional group of a linker molecule through formation of a covalent bond, or through chemisorption or physisorption via van der Waals or electrostatic or inonic interactions or hydrogen bondings or fluorous phase formation. In general each type of chemical attachment so that one binding partner binds to a further binding partner is included. This is to be understood that both chemical partners are attached to each other without any precondition to the respective binding capabilities of each respectively attached molecule. For instance, the functional group is attached to the capture molecule is equal to the capture molecule is attached to the functional group, or to both being attached to each other.

The provided planar waveguide is of a material, to which the head group of the linker molecules can be attached. Suitable waveguide materials for the present invention are materials of high refractive index such as $Ta_2O_5$, $TiO_2$, $Nb_2O_5$ or $Si_3N_4$ for which thin film deposition technologies are available for preparation of smooth optical films with waveguiding properties. An efficient production process for high refractive index waveguides on glass and polymer substrates in which an optical grating coupler is formed, is explained in detail in "Fattinger et al., Bidiffractive grating coupler: Universal transducer for optical interface analytics", OPTICAL ENGINEERING, Vol. 34 No. 9, page 2744-2753, September 1995. The planar waveguide may comprise multiple layers in which at least one is of a high refractive index. The provided planar waveguide has a high refractive index relative to the medium on the outer surface forming the upper side of the planar waveguide. For example, the refractive index of the planar waveguide may be in the range of 1.7 to 2.8, whereas the refractive index of the medium at the surface of the planar waveguide is typically in the range of 1 to 1.5, in particular 1.33-1.4 for water or aqueous assay buffer and 1 for air. Coherent light is coupled through an optical coupler into the planar waveguide so as to propagate with an evanescent field at the outer surface of the waveguide. The evanescent field penetrating out of the outer surface is diffracted at target samples bound along a plurality of predetermined lines at the outer surface of the waveguide. The thickness of the waveguiding film is preferentially in the range from 60 to 200 nm. The penetration depth of the evanescent field into the medium at the outer surface of the waveguide is preferentially smaller than 150 nm.

In a first variant of the method, the above-described step of sequentially applying the at least one plurality of linker molecules consists of applying only two pluralities of linker molecules. The two pluralities of linker molecules assemble to form two individual layers of linker molecules one above the other starting from the outer surface of the planar waveguide.

According to an aspect of the first variant, the method further comprises the following steps. Attach complementary functional groups of capture molecules to the functional groups arranged along the plurality of predetermined lines. Each capture molecule is capable of binding a target sample. Then expose the photo-labile protecting groups arranged between the plurality of predetermined lines to light of the predetermined wavelength to remove the exposed photo-labile protecting groups from the functional groups to make these functional groups capable of attaching a complementary functional group of a said further molecule. Thereafter attach complementary functional groups of modified capture molecules to the functional groups arranged between the plurality of predetermined lines. Each modified capture molecule is chosen to be incapable of binding to the target sample to which the first capture molecules are capable of binding.

The exposure of the photo-labile protecting groups arranged between the plurality of predetermined lines (second exposure) is carried out for the entire layer at which the remaining photo-labile protecting groups are arranged, without shadow regions. In fact, photo-labile protecting groups arranged between the plurality of predetermined lines are the only remaining photo-labile protecting groups after the first photo-lithographic exposure of the photo-labile protecting groups arranged along the plurality of predetermined lines. The modified capture molecules are molecules at which the coherent light scatters similarly compared to the capture molecules. Advantageously, light scattered from capture molecules and modified capture molecules has matched amplitudes and a difference in optical path length so as to destructively interfere in a predetermined detection location. Thus, the minimum signal in the predetermined detection location can be adjusted by varying the respective exposure time which relates to the amount of functional groups from which the photo-labile protecting groups are removed. The minimum signal is of advantage insofar as after the application of the target samples, the change of the signal in the detection location is mainly due to the target sample bound to the capture molecules. Thereby the contribution of the target sample to the signal in the detection location is increased compared to the signal from capture molecules without target samples, i.e. compared to the light scattered at the capture molecules alone. The capture molecules or the modified capture molecules are applied to the outer surface of the waveguide by immersion, dipping, spotting, printing or the use of a fluidic apparatus, etc.

In a second variant of the method, in the above described step of sequentially applying the at least one plurality of linker molecules consists of applying only one plurality of linker molecules.

According to an aspect of the second variant, the method further comprises the step of attaching head groups of a further plurality of linker molecules (which are preferably already bound to capture molecules via functional groups, partially or fully) as a said further molecule having a complementary functional group to the functional groups of the preceding layer of linker molecules (with deprotected functional groups) arranged along the plurality of predetermined lines. The functional groups of linker molecules of the further plurality of linker molecules are unbound (in the present variant, the linker molecules of the further plurality of linker molecules actually never have bound to photolabile protecting groups) to photo-labile protecting groups and are capable of attaching a complementary functional group of a further molecule. The linker molecules of the further plurality of linker molecules are different from the linker molecule of the preceding layer so as to provide different characteristics, like flexibility, hydrophilicity, minimum non-specific binding and optimal length for immobilization of the capture molecules on the outer surface of the planar waveguide. After this step, the linker molecules of the further plurality of linker molecules and the capture molecules bound to the further plurality of linker molecules are arranged along the plurality of predetermined lines only.

According to another aspect of the second variant, the method further comprises the following steps. Attach complementary functional groups of capture molecules to the functional groups of linker molecules of the further plurality of linker molecules arranged along the plurality of predetermined lines. (This can be achieved via applying the linker molecules together with the capture molecules.) Then exposing those photo-labile protecting groups arranged between the plurality of predetermined lines to light of the predetermined wavelength to remove the exposed photo-labile protecting groups from the functional groups to make these functional groups capable of attaching a complementary functional group of a further molecule. Thereafter attaching complementary functional groups (head groups) of another further plurality of linker molecules to the functional groups of the preceding layer of linker molecules which are arranged between the plurality of predetermined lines. The functional groups of linker molecules of the further plurality of linker molecules are unbound—actually never have bound—to photo-labile protecting groups and are capable of attaching a complementary functional group of a further molecule. Thereafter, attach complementary functional groups of another further plurality of modified capture molecules as a further molecule having a complementary functional group to the functional groups of linker molecules of the further plurality of linker molecules arranged between the plurality of predetermined lines.

In this second variant, the same advantages are achieved as in the first variant, in particular with respect to the destructive interference of light scattered from capture molecules and modified capture molecules in a predetermined detection location. It is of advantage if the application of the further plurality of linker molecules is carried out together with the application of capture molecules or the modified capture molecules. This provides the advantage that the capture molecules and the modified capture molecules can be applied partially enclosed by the further linker molecules. In this way linker molecules can provide a loosely packed matrix (e.g. a polymer such as DEXTRAN or poly(ethylene glycol) (PEG)) in which the capture molecules are embedded. The advantages thereof are discussed in detail below.

According to one aspect of the invention, the step of exposing those photo-labile protecting groups arranged along a plurality of predetermined lines is carried out for a first exposure time, and then the step of exposing those photo-labile protecting groups arranged between the plurality of predetermined lines is carried out for a second exposure time. The first exposure time is different compared to the second exposure time. In general, the exposure time is related to the amount of photo-labile protecting groups removed from the functional groups of the plurality of linker molecules. This determines the total number of functional groups capable of attaching a complementary functional group of a further molecule, like capture molecules. The number of capture molecules bound to the functional groups determines the signal of the light scattered into the detection location. Thus, the first and second exposure time determines the relative contribution of the light scattered at capture molecules arranged along the plurality of predetermined lines compared to those arranged between the plurality of predetermined lines. Since the contribution of both interferes destructively, the detected signal can be adjusted to a minimum by varying the two exposure times independently.

The maximum exposure time corresponds to a maximum exposure energy dose which is chosen to be between 1 and 10 Joules/cm$^2$, so as to separate photo-labile protecting groups along lines having a width less than half of the distance of the predetermined lines. Preferably, the first exposure dose and the second exposure dose are less than 2 Joules/cm$^2$, resulting in an exposure time when using a standard LED light source of around 390 nm wavelength of less than 60 seconds or more preferred between 1 and 10 seconds. This exposure dose has shown to be suitable for removing photo-labile protecting groups from functional groups as photocleavable linker molecules with diarylsulphid —NPPOC backbone for transient bioconjugate synthesis in high yield and with minimum side reactions.

In yet another example, sensitization of the photodeprotection as in D. Wöll, S. Walbert, K.-P. Stengele, T. Albert, T. Richmond, J. Norton, M. Singer, R. Green, W. Pfleiderer, U. E. Steiner, Triplet-sensitized photodeprotection of oligonucleotides in solution and on microarray chips, Helv. Chim. Acta 2004, 87(1), 28-45 may be useful to accomplish the photodeprotection step at the desired wavelength by means of triplett-triplett FRET energy transfer upon irradiation.

In an advantageous aspect, the step of exposing those photo-labile protecting groups arranged along the plurality of predetermined lines comprises the following steps. Dispose a phase mask in the proximity of the outer surface of the planar waveguide carrying the photo-labile protecting groups. The phase mask has a plurality of protrusions which are of a material of a first refractive index $n_1$, the first refractive index $n_1$ being different compared to a second refractive index $n_2$ of a medium present between the phase mask and the outer surface of the planar waveguide (respectively the outermost layer of linker molecules). Transmit light of the predetermined wavelength through the phase mask for exposing those photo-labile protecting groups arranged along the plurality of predetermined lines.

Such a phase mask comprises a glass substrate and a plurality of protrusions which are preferably made of a suitable material of high refractive index such as $Ta_2O_5$, $TiO_2$, $Nb_2O_5$ or $Si_3N_4$. The phase mask is for example a binary diffractive phase mask. Each of such protrusion has a predetermined depth and a predetermined distance to the adjacent protrusions so as to provide a phase shift of $\pi$ (i.e. half the wavelength) for light propagating through the protrusions of the phase mask compared to the light propagating through the liquid medium between the protrusions of the phase mask. The interface of light propagating through the phase mask creates an interference pattern with minimum light intensity along the edges of the protrusions. Thus, the interference pattern behind the phase mask is a periodicity doubled dark-bright pattern compared to the local periodicity of the protrusions in the phase mask. The width and the form of the protrusions can vary along the phase mask. The photo-lithographic illumination includes holographic methods as described in detail in Suleski, et al., "Fabrication of high-spatial-frequency gratings through computer-generated near-field holography," Optics Letters, vol. 24, No. 9, pp. 602-604, May 1, 1999. Because of holographic methods, like near-field holography, can be used to generate (or to arrange) the plurality of predetermined lines, the term "mologramm" has been coined which refers to binding sites to which a target sample may bind, which are arranged along a plurality of predetermined lines. As an example, the plurality of predetermined lines can be referred to as Mologram A and the lines located in-between the lines of the plurality of predetermined lines can be referred to as Mologram B. In useful applications, light impinging onto a detector diffracted at Mologram A is phase shifted by π (i.e. half the wavelength) compared to light diffracted at Mologramm B. Additionally, the phase mask can be coated to improve the quality of the interference pattern, as described in detail in Pasi Laakkonen et al., Coated phase mask for proximity printing of Bragg gratings, Optics Communications 192 (2001) 153-159, ELSEVIER. The light used for transmitting exposure of the photo-labile protecting groups through the phase mask is for example of 390 nm wavelength. The use of other wavelength may be required, depending on the photo-labile protecting groups to be removed from the functional groups. It is to be understood, that the exposure may either be suitable for direct photochemical attachment (e.g. using Benzophenone- or Arylazide- or Diazirin-mediated photo-radical insertion reactions or sensitization by radical initiators like Thioxanthones). In principle, the dimensions of the protrusions have to be chosen according to those wavelengths.

It is preferred, that the plurality of linker molecules of which the head groups attach to the outer surface of the waveguide assemble to form an individual layer having a thickness of 0.5 nm to 10 nm outgoing from the outer surface. The average density of the linker molecules in the first layer is chosen so as to prevent contact of the further applied molecules to the outer surface of the waveguide. This is important to prevent, for example, non-specific binding of the capture molecules and further molecules in the applied samples to the outer surface of the waveguide.

The first layer of linker molecules attach directly onto the outer surface of the planar waveguide. Advantageously, the first layer is of a high density and of a low height. Ideally, the first layer covers the outer surface such that a contact by any further molecules to the outer surface is impossible.

In an advantageous aspect, the plurality of linker molecules of which the head groups attach to the outer surface of the waveguide assemble to form a monolayer of linker molecules. The quality of the signal of diffracted light in the detection location is increased when the first layer is orderly arranged on the outer surface which provides a very small and even background of light scattered at the linker molecules at the outer surface of the waveguide. The plurality of linker molecules which form the first layer is preferentially a self-assembled monolayer (SAM). A SAM may carry the photo-labile protecting groups so as to be capable of photo-lithographical processing.

In one embodiment, the SAM may consist of a mixture of Alkanes, carrying between 10 and 100% amino groups as functional groups, which in turn may be modified by a photoprotective group either before formation of the SAM or after formation of the SAM, to generate the desired SAM ready for photo modulation according to the invention.

In another embodiment, the SAM may consist of a mixture of Alkanes, carrying between 10 and 100% carboxy groups as functional groups, which in turn may be modified by a photoprotective group either before formation of the SAM or after formation of the SAM, to generate the desired SAM ready for photo modulation according to the invention.

In another aspect of the invention, the plurality of linker molecules of which the head groups attach to the functional groups of the preceding layer of linker molecules assemble to form the uppermost individual layer having a thickness of 10 nm to 200 nm. The local average density of linker molecules per area is chosen to be low so as to allow capture molecules to diffuse therethrough or that the capture molecules are partially enclosed therein. It is preferred that the uppermost layer comprises linker molecules which are long compared to the molecules of the first layer. The uppermost layer should be of a low spatial density to allow the molecules in the target sample to laterally diffuse therethrough. These linker molecules can be flexible so as to be capable of adapting the shape. These linker molecules consist in an advantageous example a loosely packed matrix (a polymer such as a poly saccharide like dextrane, carboxymethylated dextrane, carboxymethylated hyaluronic acid, hyaluronic acid, and alginic acid, or polylactic acid, polyacrylic acid or a hydrophilic 3D-acrylate polymer for example described by D. Kyprianu et al, Talanta 103. 2013, 260-266 or a poly(ethylene glycol) (PEG) or a single stranded DNA oligonucleotide.

The polymers may further be modified to generate backbone modified polymer networks, in which the backbone modifications may consist of ionic groups, lipids, peptides oligonucleotides and the like.

In another aspect of the method, the plurality of predetermined lines are arranged in at least two separate diffraction spots at the outer surface of the planar waveguide. Each diffraction spot has an area larger than 25 $(\mu m)^2$ $((\mu m)^2 = \mu m^2)$. The plurality of predetermined lines has a distance between adjacent lines less than 1.5 µm, in particular less than 1 µm. This provides diffraction spots for the detection of light scattered thereon which have a minimum size for providing a signal of adequate intensity to be detected. The plurality of predetermined lines has a maximum distance between adjacent lines which is determined by the light which is diffracted at the diffraction spots. Preferred is the use of visible light. This distance includes harmonics of the predetermined wavelength for which the distance between adjacent lines is a multiple of the wavelength of the light propagating through the planar waveguide.

The invention provides furthermore a planar waveguide having an outer surface prepared according to a method described herebefore. A plurality of predetermined lines are arranged in at least two separate diffraction spots at the outer surface. Each diffraction spot has an area larger than 25 $\mu m^2$. The plurality of predetermined lines has a distance between adjacent lines less than 1.5 µm, in particular less than 1 µm. Preferably, a planar waveguide is provided with a plurality of diffraction spots, i.e. 100, 10000, 100000, . . . , up to $4 \times 10^6$ diffraction spots per square centimeter. The advantages described for the method are similarly provided with the planar waveguide.

According to an aspect, each plurality of predetermined lines are curved and arranged with a decreasing distance between adjacent lines in the direction of propagation of the light coupled to the planar waveguide through an optical coupler. The arrangement of curved lines with a decreasing distance between adjacent lines focuses (and interferes) the light scattered at target samples into a predetermined detection location (comparable to a phase grating lens). According to an alternative arrangement, the plurality of predetermined lines are straight and arranged under an angle relative to the direction of propagation of the light coupled into the waveguide. The alternative arrangement of the plurality of predetermined lines under an angle relative to the direction of propagation of the light fulfils the requirements for constructive interference in predetermined directions (comparable to Bragg diffraction). The plurality of predetermined straight lines causes the light to diffract in the plane of the planar waveguide. The light diffracted within the planar waveguide is coupled out of the planar waveguide via a further optical coupler (phase grating lens) into a detection location.

According to a further aspect of the invention, a kit provides a planar waveguide as described herebefore and a phase mask for preparing an outer surface of the planar waveguide. The phase mask allows to carry out a lithographic method as described herein. Such a kit may further comprise chemical, pharmaceutical and/or biological reagents suitable for the preparation of the outer surface of the planar waveguide according to a method as described herebefore. This reagents may vary in different kits.

Further advantageous aspects of the invention become apparent from the following description of embodiments of the invention with reference to the accompanying drawings in which.

Figure 1:
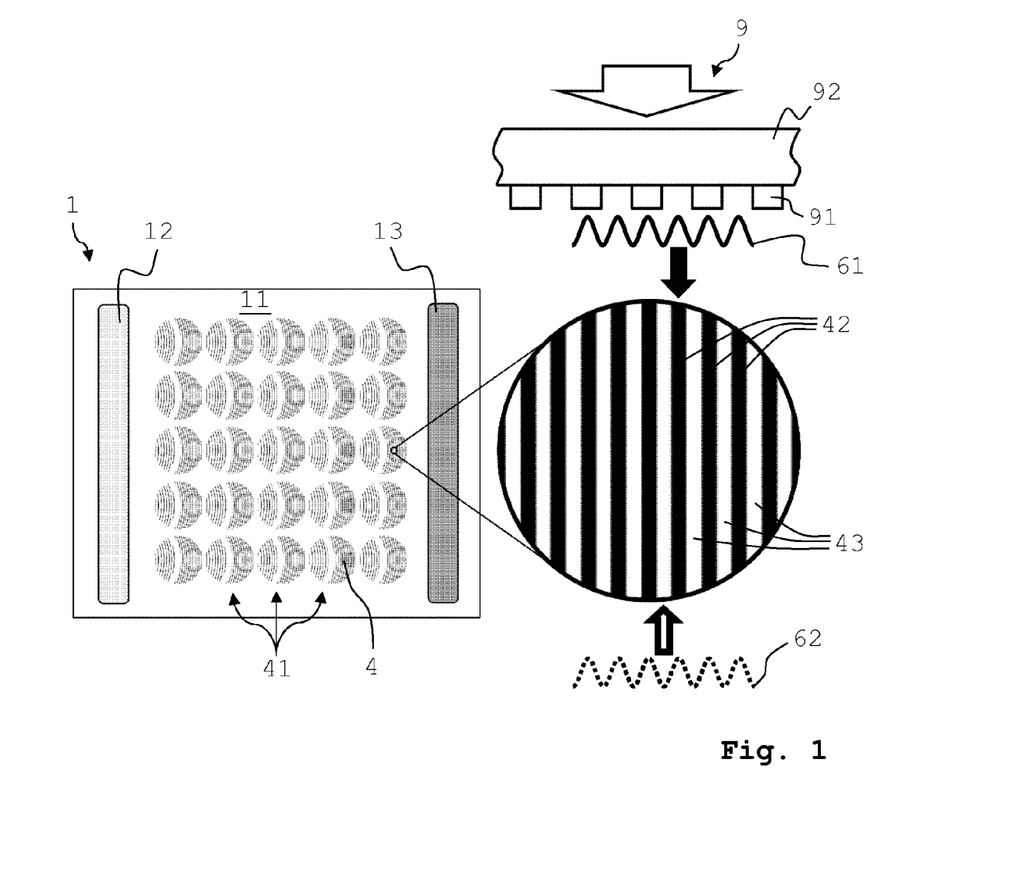
FIG. 1 shows an embodiment for a planar waveguide with an enlarged detail of a plurality of predetermined lines and a portion of a photo-lithographic mask.

FIG. 1 shows a perspective view of an example for a planar waveguide 1 having an outer surface 11 at which linker molecules can be arranged according to the invention. Structurally, the planar waveguide 1 is arranged on top of a substrate (not shown) and comprises a number of 25 separate diffraction spots 41 arranged on outer surface 11. A plurality of predetermined lines 4 (each of the shown lines represents a multiplicity of lines) is arranged in each of this diffraction spots 41. Lines 4 in the shown example are curved, but can be straight in another variant. Lines 4 in the present example have a distance between adjacent lines 4 which decreases from left to right (direction of the light propagating through the planar waveguide) to improve the detected signal. Alternatively, lines 4 can be equidistantly arranged or different pluralities of predetermined lines 4 can be arranged in said diffraction spot 41. Moreover, an optical coupler 12 and a further optical coupler 13 are arranged at planar waveguide 1 for coupling coherent light into, respectively out of, the planar waveguide 1. Both can be formed at the surface of a substrate made of glass or a polymer material. Further optical coupler 13 can alternatively or additionally be a light absorbing means. According to the working principle of a device for detecting binding events which comprises the shown planar waveguide 1, coherent light is coupled through optical coupler 12 into planar waveguide 1 so as to propagate with an evanescent field at outer surface 11. The evanescent field of the coherent light is scattered at molecules (linker molecules, capture molecules, target samples, etc.) arranged on outer surface 11 along the plurality of predetermined lines 4 such that the scattered coherent light constructively interferes in a predetermined detection location (not shown).

The shown circle provides an exaggerated view of a few of the plurality of predetermined lines 4 arranged in such a spot 41 with black lines 42 and with white lines 43 in between.

Along black lines 42, capture molecules are arranged at functional groups of the linker molecules. Capture molecules are capable of binding a target sample (the molecules are not shown in the present illustration because of the small size compared to the size of the device). White lines 43 comprise the modified capture molecules which are incapable of binding the target sample which the capture molecules are capable of binding. An evanescent field of a coherent light coupled into the planar waveguide 1 scatters at the molecules arranged at the shown black lines 42 as well as at the white lines 43. The light scattered by molecules arranged at the black lines has a first optical path length with respect to a detection location (not shown) so as to interfere to a maximum in intensity therein. Coherent light scattered at molecules arranged at the plurality of white lines 43 in between the black lines 42 has a second optical path length with respect to the detection location so as to interfere to a maximum in intensity therein. Both maxima have a phase shift of $\pi$ relative to each other so as to destructively interfere to a minimum in overall intensity. This allows to minimize background signal from the light scattered other than the target samples bound to the capture molecules. The minimum signal can be adjusted by varying the exposure time for deprotecting the respective functional groups, to which the capture molecules and modified capture molecules can bind. Theoretically, capture molecules arranged to the black lines 42 and the modified capture molecules arranged to the white lines 43 provide no overall background signal of the light scattered thereon in the single detection location, before a target sample is applied.

Above the circle providing the exaggerated view, a portion of a phase mask 9 is shown to explain the photo-lithographic illumination of those photo-labile protecting groups arranged along the plurality of predetermined lines 4. Phase mask 9 comprises a glass substrate 92 and a plurality of protrusions 91 made of a material of high refractive index such as $Ta_2O_5$, $TiO_2$, $Nb_2O_5$ or $Si_3N_4$. The thickness (or depth) of the protrusions 91 is chosen corresponding to a first refractive index $n_1$ of the material of the protrusions 91 (e.g. $Ta_2O_5$) and to a second refractive index $n_2$ of the medium present between the phase mask 9 and the outer surface 11 of the planar waveguide 1 so as to provide a predetermined phase shift. The first refractive index $n_1$ of $Ta_2O_5$ is at a wavelength of 390 nm $n_1=2.246$. In use, phase mask 9 is arranged with the protrusions 91 in the proximity of the outer surface 11 so as to expose those photo-labile protecting groups arranged along the plurality of predetermined lines 4 via near-field illumination. The linker molecules with those photo-labile protecting groups (not shown because of comparably small size) are applied to outer surface 11 in a solution of e.g. DMSO with 5% water so as to fill the space between the outer surface 11 and the phase mask 9. The second refractive index $n_2$ of the DMSO solution can be estimated as follows. DMSO has a refractive index at a wavelength of 590 nm of $n_2=1.477$. The calculated refractive index for a wavelength of 390 nm is $n_2=1.50$, as explained in detail in Kozma, J. Opt. Soc. Am. B, 22(7), p 1479 (2005). The approximated refractive index for DMSO with 5% water for 390 nm is $n_2=1.494$, as explained in detail in Le Bel and Goring, J. Chem. Eng. DATA 7(1), p 100 (1962). According to a variant N-Methyl-2-pyrrolidone (NMP) can be used as a solution for applying the molecular linkers and those photo-labile protecting groups. The phase mask 9 causes a phase shift for the light propagating through the protrusions 91 compared to the light propagating through the medium between phase mask 9 and outer surface 11. Interference causes a frequency doubled dark bright pattern compared to the pattern of the phase mask 9. The height of the protrusions 91 is chosen for $Ta_2O_5$ to be d=259 nm (d=$\lambda$/2 ($n_{Ta2O5}-n_{DMSO}$)). The width of the protrusions 91 can vary in the spot 41 for example along the direction of propagation of the light through the planar waveguide 1. The width of the protrusions 91 is preferably chosen equal or proximate to the distance of the predetermined lines 4; 42, 43 at the outer surface 11 of the planar waveguide 1. The photo-lithographic illumination of those photo-labile protecting groups is carried out by disposing phase mask 9 in the proximity thereto and illuminating these photo-labile protecting groups arranged along black lines 42 with light transmitted through phase mask 9. The exposure through phase mask 9 is carried out for a first exposure time. The second exposure of those photo-labile protecting groups arranged along the white lines 42 in between the plurality of black lines 42 is carried out without phase mask 9.

The shown solid profile 61 above the black lines 42 and dotted profile 62 below the white lines 43 represent the light intensity profile (or the interference pattern) in the near field of the light transmitted through the phase mask 9. Both profiles can moreover be interpreted to represent the local average density of capture molecules or deprotected functional groups (black lines 42) and modified capture molecules (white lines 43) bound to the respectively exposed functional groups of linker molecules. In the ideal case mentioned further above, the light scattered at capture molecules arranged on black lines 42 as well as at modified capture molecules arranged in between the black lines 42 along the white lines 43 contributes in the detection location to a minimum (ideally zero) background signal. This is theoretically achieved by identical local average densities of capture molecules and modified capture molecules. The sharp edges between black lines 42 and white lines 43 approximate the sinusoidal transition between the black and white lines (because of formal requirements such shaded illustration is not shown, but would be more realistically). In principle, the local density of capture molecules is caused by a sinusoidal intensity profile of the near field illumination through phase mask 9.

A first embodiment and a second embodiment of the method are shown hereafter, both enabling to carry out the invention. Both embodiments employ a planar waveguide as exemplified in FIG. 1. In these embodiments, the photo-lithographic step is carried out in the same manner, but in different steps. In practice, the exposure of those photo-labile protecting groups is carried out only one time by using the photo-lithographic mask. The re-alignment of the photo-lithographic mask is difficult and impractical so that the second exposure is an exposure of the remaining photo-labile protecting groups which is carried out without using a mask.

In the following FIG. 2 to FIG. 10, the first embodiment of the method according to the invention is explained.

Figure 2:
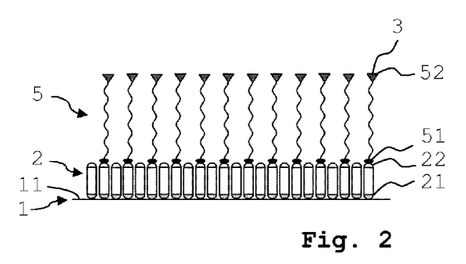
FIG. 2 shows a side view of a section of a planar waveguide such as exemplified in FIG. 1 with two pluralities of linker molecules applied thereto.

FIG. 2 shows the application of a plurality of linker molecules 2 and of a further plurality of linker molecules 5 which are subsequently applied starting from an outer surface 11 of a planar waveguide 1 so as to assemble in two separate individual layers. Linker molecules 2 of the plurality of linker molecules 2 being directly assembled on outer surface 11 to form a self-assembled monolayer (SAM). These linker molecules 2 comprise a head group 21 (e.g. $-(PO_3)^{2-}$, $-(O-PO_3)^{2-}$, trialkoxysilane or poly(L-lysine) for attaching to outer surface 11 and a functional group 22 capable of attaching a complementary functional group of a further molecule. Suitable linker molecules 2 for formation of a self-assembled monolayer (SAM) on transition metal oxides e.g. $Ta_2O_5$, $TiO_2$, $Nb_2O_5$ are e.g. the $NH_2$-terminated self-assembling molecule amino-dodecyl-phosphonate ($NH_2-(CH_2)_{12}-(PO_3)H_2$), the COOH-terminated self-assembling monolecule carboxy-pentadecyl-phosphate ($COOH-(CH_2)_{15}-$ ($PO_4$)$H_2$) or the OH-terminated self-assembling monolecule hydroxy-dodecyl-phosphate ammonium salt (OH—($CH_2$)$_{12}$—($PO_4$)($NH_4$)$_2$). (cf. Samuele Guido Pio Tosatti: FUNCTIONALIZED TITANIUM SURFACES FOR BIOMEDICAL APPLICATIONS: PHYSICO-CHEMICA CHARACTERIZATION AND BIOLOGICAL IN VITRO EVALUATION, DISS. ETH NO. 15095). The functional group 22 can be an ordinary functional group, an organic or peptidic metal chelate adsorbent, a single stranded DNA, a protein receptor or its ligand. The further molecule is not limited to specific types of molecules but is in the shown case, a loosely packed matrix (e.g. polymer such as dextrane or poly(ethylene glycol) (PEG)) functionalized with a complimentary functional group (head group) 51 (e.g. an ordinary functional group like a carboxy of the linker molecules 5 of the subsequently applied plurality of linker molecules 5. Also the linker molecules 5 of the subsequently applied plurality of linker molecules 5 comprise head groups 51 capable of attaching to the functional groups 22 of the previously applied layer. The functional groups 52 are capable of attaching a complementary functional group of a further molecule. The functional groups 52 are in the shown case protected by a photo-labile protecting group 3. The photo-labile protecting group 3 protects the functional group 52 such that no complementary functional group of a further molecule, like a capture molecule, can bind thereto.

Therefore the functional groups 52 are limited to functional groups capable of being protected by a photolabile protecting group like amino-, mercapto-, hydroxyl, carboxylate group.

Figure 3:
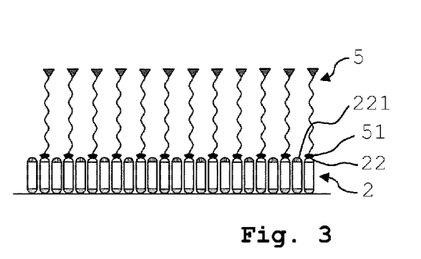
FIG. 3 shows the planar waveguide of FIG. 2 illustrating a step of deactivating the functional groups to which no linker molecule of the further plurality of linker molecules has bound.

In FIG. 3, the functional groups 22 of the plurality of linker molecules 2 to which no head group 51 of the further plurality of linker molecules 5 has bound are deactivated, eg by reacting with a further molecule which comprises no functional group which is capable of reacting or interacting with a further molecule with a complementary functional group. The deactivated functional groups 221 are incapable of any further binding.

Figure 4:
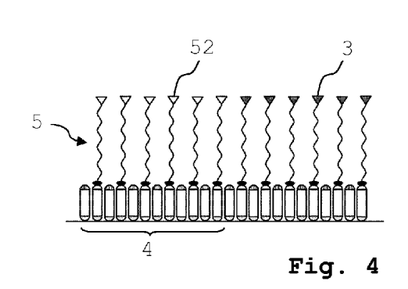
FIG. 4 shows the planar waveguide of FIG. 3 illustrating a step of exposing those photo-labile protecting groups arranged along a plurality of predetermined lines to light.

In FIG. 4, those photo-labile protecting groups 3 bound to the functional groups 52 of the further plurality of linker molecules 5 arranged along a plurality of predetermined lines 4 are exposed to light and are removed from the functional groups 52. Thus, the functional groups 52 arranged along a plurality of predetermined lines 4 are capable of attaching a complementary functional group of a further molecule, like a capture molecule, and the functional groups 52 arranged between the plurality of predetermined lines 4 carry photo-labile protecting groups 3. The exposure can be achieved photo-lithographically as explained for FIG. 1 by means of a phase mask. The shown single line 4 exemplifies one line of the plurality of predetermined lines 4 along which those photo-labile protecting groups 3 are exposed to light.

Theoretically, this state of the method provides a planar waveguide which can be used for the detection of binding events. For example, if a applied target sample binds directly to the functional groups of the plurality of linker molecules arranged along the plurality of predetermined lines.

Figure 5:
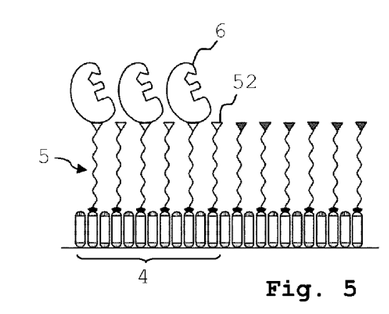
FIG. 5 shows the planar waveguide of FIG. 4 illustrating a step of applying a plurality of capture molecules.

In FIG. 5, a plurality of capture molecules 6 is applied to the functional groups 52 arranged along the plurality of predetermined lines 4. In general, such a capture molecule 6 is any molecule capable of simultaneously binding to the functional group 52 of the molecular linker 5 and to a target molecule in a sample (shown in FIG. 10) to be investigated. The illustrated capture molecules 6 represents a protein with two biding sites for binding the target molecule in a sample. The linker molecules 5 might be loosely packed with space between the linker molecules that can be filled with capture molecules 6. In this case, the capture molecules 6 are preferentially embedded within the a loosely packed plurality of linker molecules 5. Advantageously, such a plurality of loosely packed linker molecules 5 consists of a loosely packed matrix (e.g. a polymer such as DEXTRAN or poly(ethylene glycol) (PEG)) that has no or minimal nonspecific interaction with the capture molecule 6 and with the molecules in the applied sample.

Each linker molecule 5 might carry several (i.e. two or more) functional groups 52 arranged along the linker molecule 5. In this variant of the first embodiment of the method according to the invention all functional groups 52 arranged along linker molecules 5 are protected by a photo-labile protecting group before removal of protecting groups from the functional groups 52 by the first exposure to light.

Figure 6:
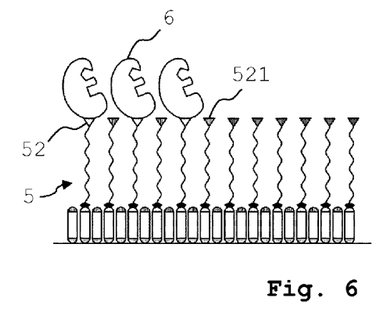
FIG. 6 shows the planar waveguide of FIG. 5 illustrating a step of deactivating the functional groups to which no capture molecule have bound.

In FIG. 6, functional groups 52 of the further plurality of linker molecules 5 to which no capture molecule 6 has bound are deactivated. The deactivated functional groups 521 are incapable of any further binding.

This provides a planar waveguide which can be used for the detection of binding events. A target sample can bind to the binding sites provided by the capture molecules arranged along a plurality of predetermined lines to scatter coherent light thereon so as to interfere in a predetermined detection location to a maximum. However, in practice a comparably strong background signal is contributed to the signal in the detection location by light scattered at the capture molecules alone, i.e. without a target sample bound to the capture molecule. A possibility to decrease the background signal relative to the detected signal is shown in the following.

Figure 7:
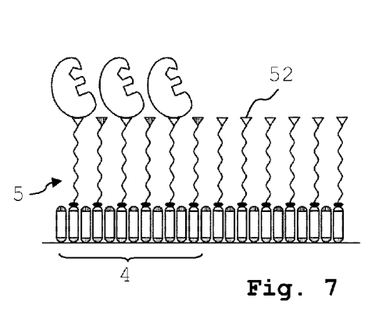
FIG. 7 shows the planar waveguide of FIG. 6 illustrating a step of exposing those photo-labile protecting groups arranged between the plurality of predetermined lines to light.

In FIG. 7, those photo-labile protecting groups are removed from the functional group 52 of the further plurality of linker molecules 5 which are arranged between the plurality of predetermined lines 4 by exposure to light. This second exposure (the first exposure is carried out through the phase mask) does not need a photo-lithographic mask because of the remaining photo-labile protecting groups are arranged properly along a plurality of predetermined lines which are formed in between the plurality of predetermined lines 4 formed in the first exposure.

Figure 8:
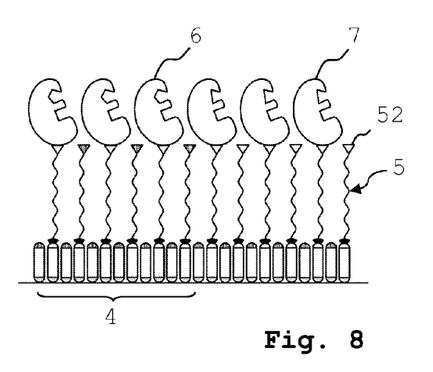
FIG. 8 shows the planar waveguide of FIG. 7 illustrating a step of applying a plurality of modified capture molecules.

In FIG. 8, a plurality of modified capture molecules 7 is applied to functional groups 52 of the further plurality of linker molecules 5 arranged in between the plurality of predetermined lines 4. The modified capture molecules 7 are in the present example a mutated protein. In general, modified capture molecules 7 are structurally similar to capture molecules 6 and have been modified by mutation or chemically so as to be incapable of binding a target molecule in a sample (not shown) to which the capture molecules 6 are capable of binding. In other words, modified capture molecules 7 have no binding site capable of binding a target sample while they scatter coherent light similarly compared to capture molecules 6.

Figure 9:
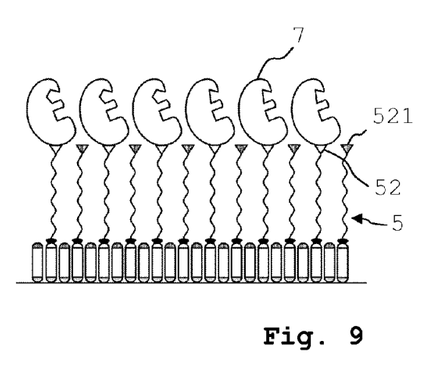
FIG. 9 shows the planar waveguide of FIG. 8 illustrating a step of deactivating the functional groups to which no modified capture molecules are bound.

In FIG. 9, functional groups 52 of the plurality of linker molecules 5 to which no modified capture molecule 7 has bound are deactivated. The deactivated functional groups 52 are incapable of any further binding.

This results in a planar waveguide which can be used in the detection of binding events. The advantage of such a planar waveguide is, as explained above, that the contribution of the scattered light from the capture molecules as well as from the modified capture molecules destructively interferes to a minimum signal. Advantageously, the minimum signal is adjusted due to changing the exposure time and consequently the number of capture molecules or modified capture molecules attached to the deprotected functional groups so as to minimize the background signal in the detection location.

Figure 10:
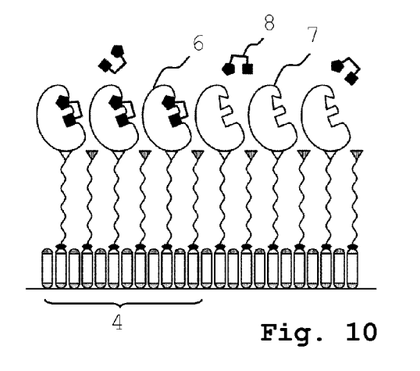
FIG. 10 shows the planar waveguide of FIG. 9 illustrating a step of applying a plurality of target samples.

FIG. 10 shows the application of a plurality of target molecules 8 in a sample to capture molecules 6 arranged along the plurality of predetermined lines 4. As can be seen, those target samples 8 do only bind to capture molecules 6. Modified capture molecules 7 are incapable of binding the target sample 8. Thus, the light in the detection location (not shown) has been minimized by adjusting the contributions of light scattered at capture molecules 6 with respect to light scattered at modified capture molecules 7. Advantageously, after application of target samples 8, changes of detected light in the detection location originate in actual binding of target samples 8 to capture molecules 6.

The detection of binding events is advantageous in that way that the coherent light is not only scattered by the capture molecules 6 arranged along the plurality of predetermined lines 4 (corresponding to the black lines 42 of FIG. 1) but is additionally scattered by the modified capture molecules 7 (corresponding to the white lines 43 of FIG. 1). Since the distance between capture molecules 6 and modified capture molecules 7 is chosen to be half the wavelength (or a multiple of the wavelength plus half the wavelength) of the coherent light, scattered light interferes theoretically in a detection location to a minimum. In practice, the contribution from the capture molecules 6 and the modified capture molecules 7 in the detection location does not interfere to zero light, but rather there will be some background light. The binding of the target sample will cause a change to said minimum signal which is comparably large with respect to the minimum background signal.

In the following FIG. 11 to FIG. 16, the second embodiment is described to explain another way to carry out the method according to the invention.

Figure 11:
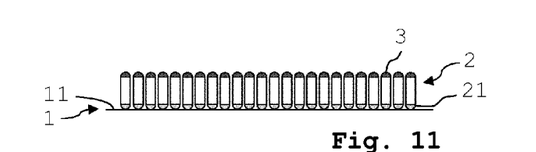
FIG. 11 shows a side view of a planar waveguide as exemplified in FIG. 1 on which the linker molecules are arranged according to a further embodiment illustrating a step applying one layer of linker molecules with photo-labile protecting groups.

In FIG. 11, a plurality of linker molecules 2 is applied to adhere with head groups 21 to the outer surface 11 of planar waveguide 1. The plurality of linker molecules 2 comprise functional groups (not shown because they are covered) protected by photo-labile protecting groups 3. The second embodiment is different compared to the first embodiment in that a single plurality of linker molecules 2 is applied (only the SAM) in the first step which carry photo-labile protecting groups 3.

Figure 12:
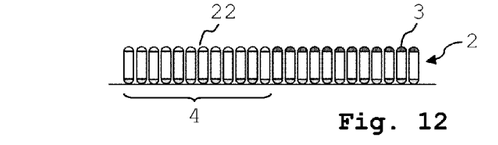
FIG. 12 shows the planar waveguide of FIG. 11 illustrating a step of exposing those photo-labile protecting groups arranged along the plurality of predetermined lines to light.

In FIG. 12, photo-labile protecting groups 3 arranged along a plurality of predetermined lines 4 are exposed to light and are removed. The exposure along the plurality of predetermined lines 4 is carried out photo-lithographically. Thus the deprotected functional groups 22 of the linker molecules 2 are arranged along a plurality of predetermined lines 4.

Figure 13:
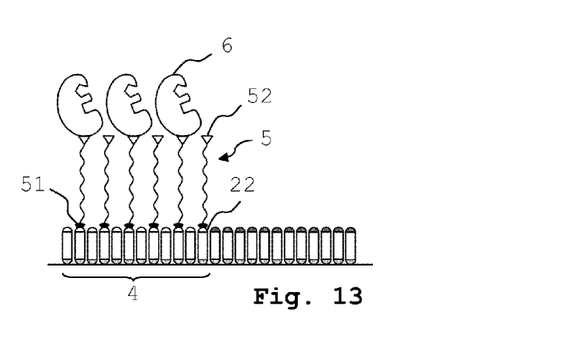
FIG. 13 shows the planar waveguide of FIG. 12 illustrating a step of applying a further plurality of linker molecules which are partially bound to capture molecules via functional groups, the further plurality of linker molecules being arranged along the plurality of predetermined lines.

In FIG. 13, a plurality of capture molecules 6 bound to functional groups 52 of linker molecules 5 are applied together (attached to each other) along the plurality of predetermined lines 4. The complementary functional group of capture molecule 6 is attached to the functional group 52 of linker molecule 5 and both together are attached via head group 51 to functional group 22. This allows in preferred examples to enclose the capture molecules 6 partially in said linker molecules 5 (e.g. the linker molecules 5 form a loosely packed matrix (e.g. a polymer such as dextran or poly(ethylene glycol) (PEG)) while allowing a target sample (not shown) to bind to the binding sites provided by capture molecules 6.

Figure 14:
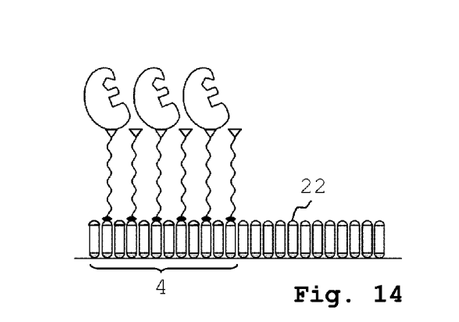
FIG. 14 shows the planar waveguide of FIG. 13 illustrating a step of exposing those photo-labile protecting groups arranged between the plurality of predetermined lines to light.

In FIG. 14, photo-labile protecting groups arranged between the plurality of predetermined lines 4 are exposed to light of predetermined wavelength (second exposure without using a photo-lithographic mask). Deprotected functional groups 22 are capable of attaching a complementary functional group of further molecules, like modified capture molecules. The minimum background signal is achieved in the second embodiment similar as explained for the first embodiment (see FIG. 7).

Figure 15:
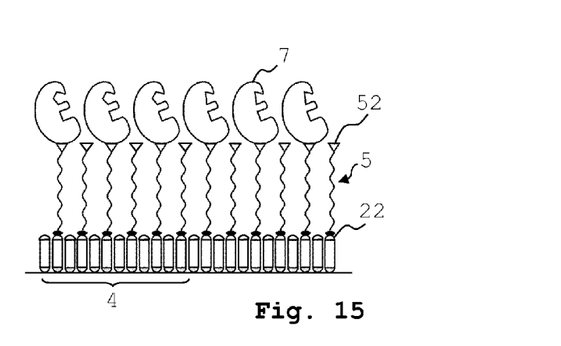
FIG. 15 shows the planar waveguide of FIG. 14 illustrating a step of applying a further plurality of linker molecules which are partially bound to modified capture molecules via functional groups, the further plurality of linker molecules being arranged between the plurality of predetermined lines.

In FIG. 15, a plurality of modified capture molecules 7 attached (bound) to functional groups 52 of linker molecules 5 is applied to functional groups 22 arranged in between the plurality of predetermined lines 4 (similar to FIG. 13).

Figure 16:
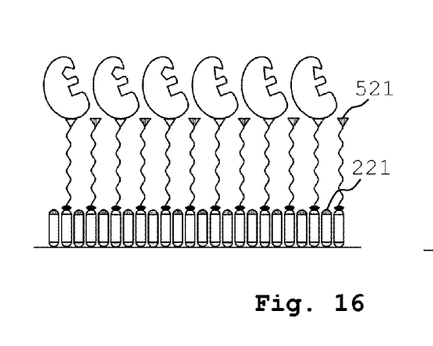
FIG. 16 shows the planar waveguide of FIG. 15 illustrating a step of deactivating the remaining functional groups of the first layer of linker molecules to which no further linker molecules are bound, the remaining functional groups of the second layer of linker molecules to which no capture molecules are bound and deactivating the remaining functional groups of the second layer of linker molecules to which no modified capture molecules are bound.

In FIG. 16, functional groups 521 to which no modified capture molecule has bound as well as functional groups 221 to which no head group of a linker molecule has bound are deactivated. This provides a prepared planar waveguide to be used as explained in FIG. 10.

Figure 17:
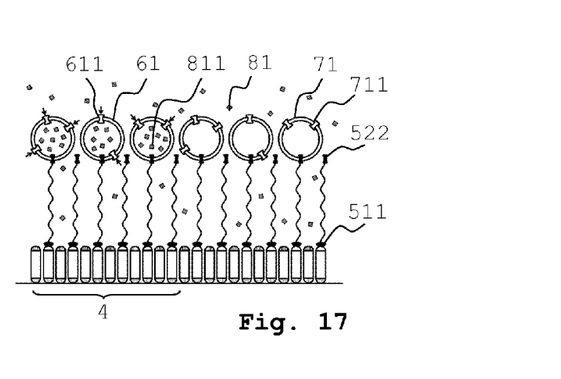
FIG. 17 shows a side view of a planar waveguide on which the molecular linkers are arranged according to another variant of the invention illustrating alternative molecular linkers and alternative capture molecules.

FIG. 17 shows another variant of the invention in which alternative molecular linkers are used having alternative head groups 511 as well as alternative functional groups 522. Membrane-like superstructures (e.g. vesicles or liposomes) 61 and modified membrane-like superstructures (e.g. modified vesicles or modified liposomes) 71 are arranged at the alternative functional groups 522. The membrane-like superstructure 61 with an incorporated or reconstituted membrane transport protein 611 (transporter or channel) represents a captive capture molecule. The modified membrane-like superstructures 71 with an incorporated or reconstituted modified membrane transport protein 711 (modified transporter or modified channel) represents a modified captive capture molecule. Corresponding to FIG. 10 and FIG. 17 membrane-like superstructures 61 and modified membrane-like superstructures 71 are arranged along a plurality of predetermined lines 4 and in between the plurality of predetermined lines 4, respectively. A target sample 81 can be captured in the captive capture molecules (captured inside the membrane-like superstructures). In this way, the term capture molecule can not only be seen as providing a number of individual binding sites to which a target sample can bind, or not, but is rather suitable to capture a target sample via a membrane transport protein. This provides a method to accumulate the captured target samples 811 over a time period for integrally detecting a target sample 81.

Figure 18:
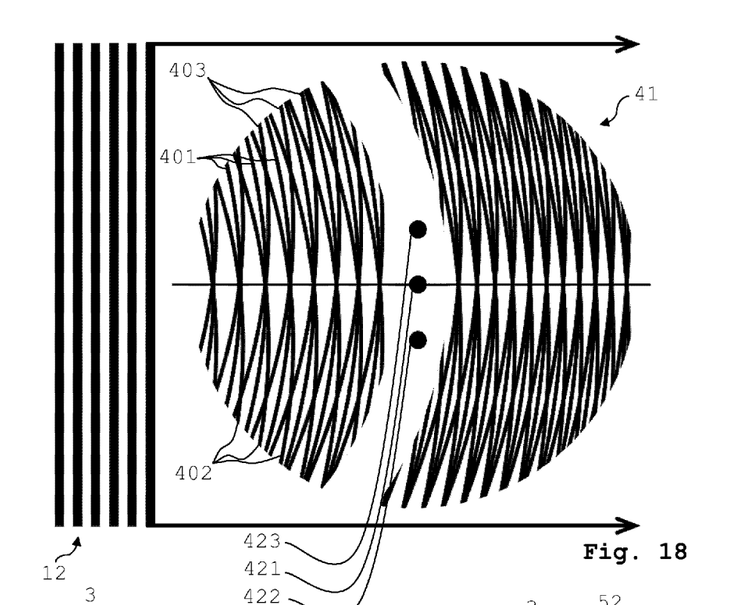
FIG. 18 shows a further aspect of the invention with three pluralities of predetermined lines arranged in a single diffraction spot, each plurality focusing the diffracted light in a different detection location.

FIG. 18 shows a further aspect of the invention. Three pluralities of predetermined lines 401, 402, 403 are arranged in one diffraction spot 41 on a planar waveguide. Each plurality being arranged such that light coupled via an optical coupler 12 into the planar waveguide diffracts at each plurality of predetermined lines 401, 402, 403 so as to constructively interfere in separate detection locations 421, 422, 423. The present arrangement of three pluralities of predetermined lines 401, 402, 403 is to be seen as an example but rather other numbers of pluralities of predetermined lines 401, 402, 403 can be arranged. The same applies for the geometry of the shown lines which is in the present example chosen to cause the light coupled via the optical coupler 12 to constructively interfere in three different detection locations 421, 422, 423 arranged along a line. The diffraction spot 41 with multiple detection locations is denoted as (or represents) a mologram with multiple foci.

A method is described in the following for applying (three) different types of capture molecules each on a different (of three) plurality of predetermined lines. This arrangement is of advantage as process cascades are detectable. For example, a target sample is split up in separate products at the first type of capture molecule so as to provide a signal in the first detection location. A first product of this reaction does then bind to the second type of capture molecules so as to provide a signal in the second detection location. A second product of the reaction binds to the third type of capture molecule so as to provide a signal in the third detection location. The attachment of the different types of capture molecules to the different predetermined pluralities of predetermined lines can be achieved, for example, by use of single stranded DNAs as described below (orthogonal chemistry). Alternatively, orthogonal photochemistry using different wavelengths for exposure and removal of the photolabile protecting groups can be carried out to achieve that only a predetermined type of capture molecule is arranged at a predetermined plurality of predetermined lines in the diffraction spot.

Figure 19:
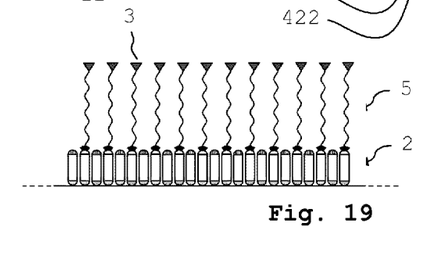
FIG. 19 shows the planar waveguide of FIG. 18 with two pluralities of linker molecules applied over a entire diffraction spot on the outer surface of the planar waveguide, the uppermost plurality carrying photolabile protecting groups.

FIG. 19 is a planar waveguide 1 having an outer surface 11 on which two pluralities of linker molecules 2, 5 are applied. The uppermost plurality of linker molecules 5 carrying photolabile protecting groups 3 (comparable to FIG. 3).

Figure 20:
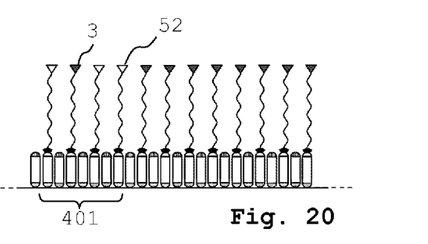
FIG. 20 shows the planar waveguide of FIG. 19 illustrating a step of partially exposing photolabile protecting groups arranged along a first plurality of predetermined lines to light.

FIG. 20 shows a step of partially exposing photolabile protecting groups 3 arranged along a first plurality of predetermined lines 401 to light. "Partially exposing" is the removal of only a number of photolabile protecting groups 3 along such a line 401. The number is high enough to provide a detectable signal of diffracted light for target samples bound to the plurality of a first capture molecule. The number should be that small that further (partial) exposures can be carried out along further pluralities of predetermined lines (402, 403) which result in the removal of further pluralities of photolabile protecting groups along further lines (402, 403) in the same diffraction spot. Such lines (401, 402, 403) can be crossed, or in other words, a number of lines can be formed above each other. With reference to FIG. 18, the crossings of the lines (401, 402, 403) contribute to the signal in different detection locations (421, 422, 423). FIG. 20 shows a possible molecular structure of a mologram with multiple foci.

Figure 21:
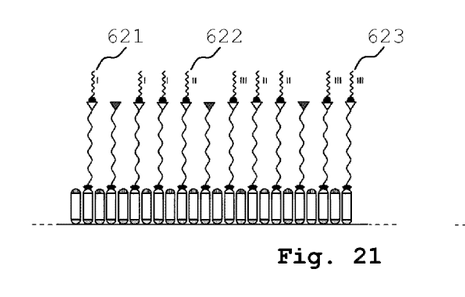
FIG. 21 shows the planar waveguide of FIG. 20 with three types of single stranded DNA subsequently applied to be arranged at three partially exposed pluralities of predetermined lines.

FIG. 21 shows three types of single stranded DNAs 621 (Type I), 622 (Type II), 623 (Type III) subsequently applied via repeating the partial exposure explained in FIG. 20 to be arranged at three pluralities of predetermined lines. The different pluralities of predetermined lines diffract the light in different foci (separated detection locations).

Figure 22:
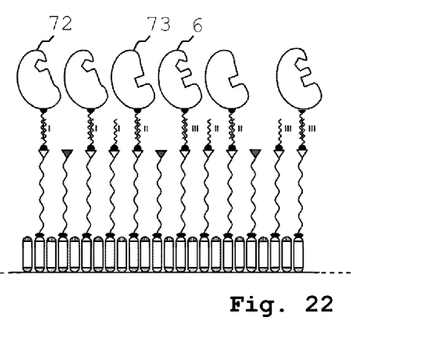
FIG. 22 shows the planar waveguide of FIG. 21 with three different types of capture molecules arranged at three different pluralities of predetermined lines.

Single stranded DNA allows to carry out orthogonal chemistry so that different capture molecules 6, 72, 73 are bound to different complementary single stranded DNAs 631, 622, 623 selectively so that only a predetermined type of capture molecule is arranged at a predetermined plurality of predetermined lines. The arrangement shown in FIG. 22 allows to individually detect the pharmaceutical, biological or chemical reactions in the respective detection location (421, 422, 423).

Figure 23:
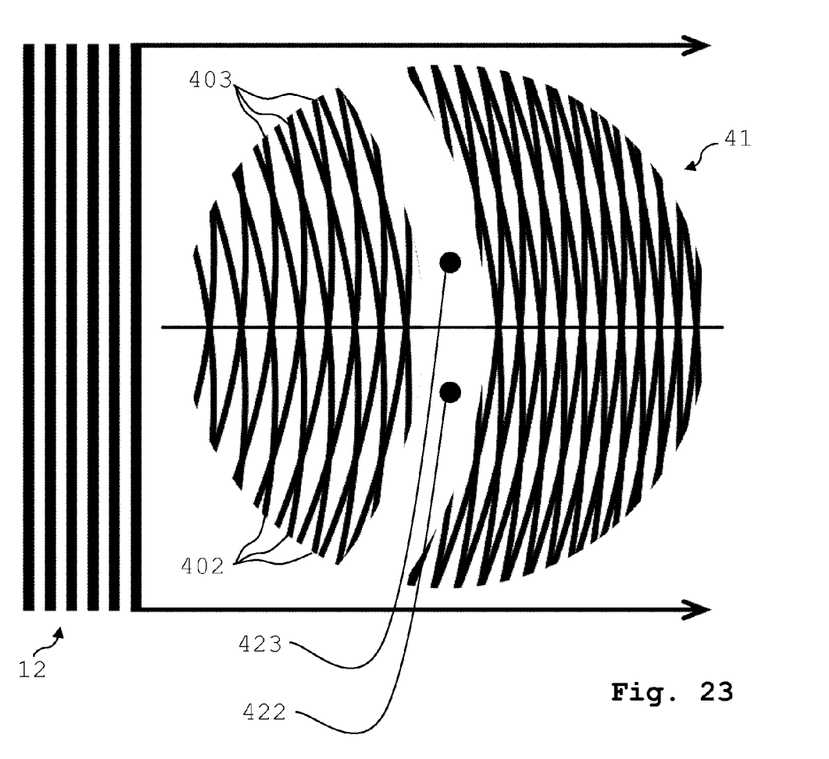
FIG. 23 shows a further aspect of the invention with two pluralities of predetermined lines arranged in a single diffraction spot, each plurality focusing the diffracted light in a individual detection location.

FIG. 23 shows a further aspect of the invention. Two pluralities of predetermined lines 402, 403 are arranged in one diffraction spot 41 on a planar waveguide (similar to FIG. 18). Each plurality being arranged such that light coupled via an optical coupler 12 into the planar waveguide diffracts at each plurality of predetermined lines 402, 403 so as to constructively interfere in separate individual detection locations 422, 423.

Figure 24:
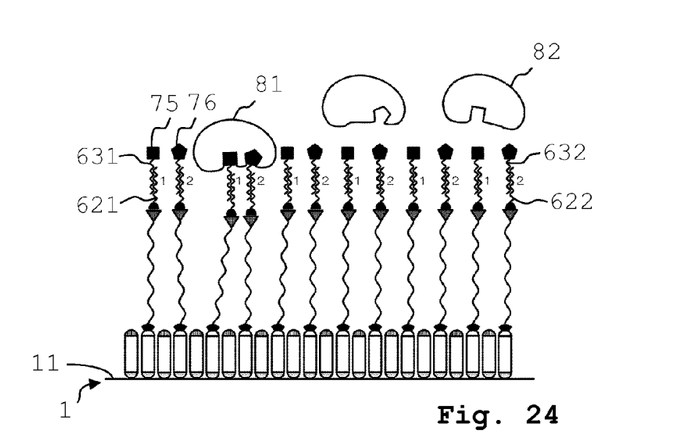
FIG. 24 shows the planar waveguide with two different types of capture molecules of a different kind compared to the foregoing examples arranged at the two different pluralities of predetermined lines of FIG. 23.

FIG. 24 is the planar waveguide 1 of FIG. 23 showing an area of the outer surface 11 in which lines of the two pluralities of predetermined lines 402, 403 intersect. Different capture molecules (in the present example molecules capable of binding to one of at least two binding sites of a protein which is applied as target sample) 75, 76 are arranged at different pluralities of predetermined lines (see FIG. 23; 402, 403) what can be achieved by orthogonal chemistry. As explained above, orthogonal chemistry uses for example different single stranded DNAs 621, 622, and corresponding complementary single stranded DNAs 631, 632 for immobilizing different types of capture molecules 75, 76 so as to be arranged at different pluralities of predetermined lines in the same diffraction spot (see FIG. 23; 41). An alternative is orthogonal photochemistry using different wavelengths for exposure of photolabile protecting groups. A target sample 81 which is a protein capable of binding to both capture molecules 75, 76 can form cooperative bindings via multiple bond interaction. Such a multiple bond interaction is of a high strength because of the combined strength of both, binding of target sample 81 to capture molecule 75, as well as, binding of the target sample 81 to capture molecule 76. Both bindings can be formed simultaneously or instantaneously within short periods of time. The multiple bond interactions are optically detected via both detection locations which provide correlated signals in both detection locations. Advantageously, this can be achieved using a time resolved detection method.

The invention claimed is:

1. A method for preparing an outer surface of a planar waveguide so as to be capable of binding target samples along a plurality of predetermined lines, the method comprising the steps of:
    providing a planar waveguide having an outer surface adapted for attachment of a linker molecule to the outer surface;
    sequentially applying at least one plurality of linker molecules to the outer surface, each plurality of the at least one plurality of linker molecules assembling to form an individual layer of linker molecules with individual layers being formed one above the other starting from the outer surface of the planar waveguide, each linker molecule comprising a functional group and a head group, the head group being capable of attaching to the outer surface of the planar waveguide or to the functional groups of the preceding layer of linker molecules, and wherein the functional groups of the linker molecules of the uppermost layer are bound to photo-labile protecting groups so that each functional group of the uppermost layer bound to a said photo-labile protecting group is incapable of attaching a complementary functional group of a further molecule; and
    exposing those photo-labile protecting groups of the uppermost layer arranged along a plurality of predetermined lines to light of a predetermined wavelength to remove the exposed photo-labile protecting groups from the functional groups to make these functional groups capable of attaching a complementary functional group of a further molecule.

2. A method according to claim 1, wherein the step of sequentially applying the at least one plurality of linker molecules consists of applying only two pluralities of linker molecules, the two pluralities of linker molecules assembling to form two individual layers of linker molecules one above the other starting from the outer surface of the planar waveguide.

3. A method according to claim 1, further comprising the steps of:
    attaching complementary functional groups of capture molecules to the functional groups of the uppermost layer of linker molecules arranged along the plurality of predetermined lines, each capture molecule being capable of binding a target sample;
    exposing those photo-labile protecting groups arranged between the plurality of predetermined lines to light of the predetermined wavelength to remove the exposed photo-labile protecting groups from the functional groups to make these functional groups capable of attaching a complementary functional group of a said further molecule; and
    attaching complementary functional groups of modified capture molecules to the functional groups arranged between the plurality of predetermined lines, each modified capture molecule being incapable of binding to that target sample to which the capture molecules are capable of binding.

4. A method according to claim 3, wherein the step of exposing those photo-labile protecting groups arranged along the plurality of predetermined lines is carried out for a first exposure dose, and wherein the step of exposing those photo-labile protecting groups arranged between the plurality of predetermined lines is carried out for a second exposure dose, the first exposure dose being different from the second exposure dose.

5. A method according to claim 4, wherein the first exposure dose and the second exposure dose are less than 10 Joules/cm².

6. A method according to claim 1, wherein the step of sequentially applying the at least one plurality of linker molecules consists of applying only one plurality of linker molecules.

7. A method according to claim 1, further comprising the step of attaching head groups of a further plurality of linker molecules to the functional groups of the preceding layer of linker molecules which are arranged along the plurality of predetermined lines, the functional groups of the linker molecules of the further plurality of linker molecules being unbound to photo-labile protecting groups and being capable of attaching a complementary functional group of a further molecule.

8. A method according to claim 7, further comprising the steps of:
attaching complementary functional groups of capture molecules to the functional groups of linker molecules of the further plurality of linker molecules arranged along the plurality of predetermined lines;
exposing those photo-labile protecting groups arranged between the plurality of predetermined lines to light of the predetermined wavelength to remove the exposed photo-labile protecting groups from the functional groups to make these functional groups capable of attaching a complementary functional group of a further molecule;
attaching complementary functional groups of another further plurality of linker molecules to the functional groups of the preceding layer of linker molecules which are arranged between the plurality of predetermined lines, the functional groups of the linker molecules of the another further plurality of linker molecules being unbound to photo-labile protecting groups and being capable of attaching a complementary functional group of a said further molecule; and
attaching complementary functional groups of modified capture molecules to the functional groups of linker molecules of the further plurality of linker molecules arranged between the plurality of predetermined lines.

9. A method according to claim 1, wherein the step of exposing those photo-labile protecting groups arranged along the plurality of predetermined lines comprises the steps of:
disposing a phase mask in the proximity of the photo-labile protecting groups, the phase mask having a plurality of protrusions having a first refractive index $n_1$, the first refractive index $n_1$ being different from a second refractive index $n_2$ of a medium arranged between the phase mask and the outer surface of the planar waveguide; and
transmitting light of the predetermined wavelength through the phase mask for exposing those photo-labile protecting groups arranged along the plurality of predetermined lines.

10. A method according to claim 1, wherein the plurality of linker molecules of which the head groups attach to the outer surface assemble to form a individual layer having a thickness of 0.5 nm to 10 nm.

11. A method according to claim 1, wherein the plurality of linker molecules of which the head groups attach to the outer surface assemble to form a monolayer of linker molecules.

12. A method according to claim 1, wherein the plurality of linker molecules of which the head groups attach to the functional groups of the preceding layer of linker molecules assemble to form the uppermost individual layer having a thickness of 10 nm to 200 nm.

13. A method according to claim 1, wherein the plurality of predetermined lines are arranged in at least two separate diffraction spots at the outer surface of the planar waveguide, each diffraction spot has an area larger than 25 $\mu m^2$ and wherein the plurality of predetermined lines has a distance between adjacent lines less than 1.5 $\mu m$, in particular less than 1 $\mu m$.

14. A planar waveguide having an outer surface prepared to be capable of binding target samples along a plurality of predetermined lines, wherein the plurality of predetermined lines are arranged in at least two separate diffraction spots at the outer surface, each diffraction spot has an area larger than 25 $\mu m^2$, and wherein the plurality of predetermined lines has a distance between adjacent lines less than 1.5 $\mu m$, in particular less than 1 $\mu m$.

15. A planar waveguide according to claim 14, wherein the plurality of predetermined lines are arranged with respect to a direction of propagation of a light coupled into the planar waveguide through an optical coupler with a decreasing distance between adjacent predetermined lines in the direction of propagation of the light or being arranged under an angle relative to the direction of propagation of the light.

16. A kit comprising a planar waveguide according to claim 14 and a phase mask for preparing an outer surface of the planar waveguide to be capable of binding target samples along a plurality of predetermined lines.

\* \* \* \* \*